US 11,350,839 B2

(12) United States Patent
Tseng et al.

(10) Patent No.: US 11,350,839 B2
(45) Date of Patent: Jun. 7, 2022

(54) NON-CONTACT SELF-INJECTION-LOCKED VITAL SIGN SENSOR

(71) Applicant: National Taiwan University of Science and Technology, Taipei (TW)

(72) Inventors: Chao-Hsiung Tseng, New Taipei (TW); Yi-Hua Lin, Changhua County (TW)

(73) Assignee: NATIONAL TAIWAN UNIVERSITY OF SCIENCE AND TECHNOLOGY, Taipei (TW)

( * ) Notice: Subject to any disclaimer, the term of this patent is extended or adjusted under 35 U.S.C. 154(b) by 358 days.

(21) Appl. No.: 16/807,338

(22) Filed: Mar. 3, 2020

(65) Prior Publication Data

US 2020/0359930 A1    Nov. 19, 2020

(30) Foreign Application Priority Data

May 13, 2019    (TW) ................................ 108116438

(51) Int. Cl.
*A61B 5/05*      (2021.01)
*H03F 3/04*      (2006.01)
(Continued)

(52) U.S. Cl.
CPC ................ *A61B 5/05* (2013.01); *A61B 5/024* (2013.01); *A61B 5/0507* (2013.01);
(Continued)

(58) Field of Classification Search
CPC ......... A61B 5/024; A61B 5/0507; A61B 5/08; A61B 5/02438; A61B 5/7228; A61B 5/05;
(Continued)

(56) References Cited

PUBLICATIONS

Chuang et al, 60-GHz Millimeter-Wave Life Detection System (MLDS) for NoncontactHuman Vital-Signal Monitoring, IEEE Sensors JL vol. 12, No. 3, Mar. 2012 (Year: 2012).*

(Continued)

*Primary Examiner* — Arnold M Kinkead
(74) *Attorney, Agent, or Firm* — WPAT, PC

(57) ABSTRACT

A non-contact self-injection-locked vital sign sensor is disclosed, which includes transmitting antenna, receiving antenna, self-injection-locked integrated circuit and demodulator. The self-injection-locked integrated circuit includes voltage-controlled oscillator, mixer, two amplifiers and harmonic-frequency power combiner. A frequency-multiplied signal is produced by amplifiers and harmonic-frequency power combiner then transmitted to a living body by transmitting antenna. A frequency-divided signal is produced by voltage-controlled oscillator and mixer then transmitted to voltage-controlled oscillator, then a frequency- and amplitude-modulated signal is produced by the voltage-controlled oscillator then transmitted to demodulator to produce a vital sign. So as to detect vital sign with a higher frequency to increase measurement sensitivity by using a low-cost integrated circuit process. A centrifugal compressor includes a volute base block, a volute cover plate, an impeller, a diffuser-adjusting assembly, a radial constraint assembly, an axial constraint assembly and a driving assembly.

10 Claims, 4 Drawing Sheets

(51) Int. Cl.
  *H01P 5/12* (2006.01)
  *H03L 7/089* (2006.01)
  *A61B 5/00* (2006.01)
  *A61B 5/113* (2006.01)
  *A61B 5/08* (2006.01)
  *A61B 5/024* (2006.01)
  *A61B 5/0507* (2021.01)
  *H03L 7/099* (2006.01)
  *H03D 7/00* (2006.01)
  *H03C 5/00* (2006.01)

(52) U.S. Cl.
  CPC ............ *A61B 5/0816* (2013.01); *A61B 5/113* (2013.01); *A61B 5/7228* (2013.01); *H01P 5/12* (2013.01); *H03F 3/04* (2013.01); *H03L 7/0891* (2013.01); *H03L 7/099* (2013.01); *A61B 5/02438* (2013.01); *A61B 5/08* (2013.01); *H03B 2200/0074* (2013.01); *H03C 5/00* (2013.01); *H03D 7/00* (2013.01); *H03L 2207/06* (2013.01)

(58) Field of Classification Search
  CPC ... A61B 5/0816; A61B 5/113; G01S 13/2491; G01S 13/88; G01S 13/583; H03B 2200/0074; H03L 7/099; H03L 2207/06; H03C 5/00; H03D 5/07; H03F 3/04; H01P 5/12
  USPC ................ 600/407; 607/101, 69, 76, 68, 30; 324/76.11, 629, 642; 331/53; 334/30; 329/307
  See application file for complete search history.

(56) References Cited

PUBLICATIONS

Wang et al, A Novel Vital-Sign Sensor Based on a Self-Injection-Locked Oscillator, IEEE Trans. on Microwave Theory and Tech, vol. 58, No. 12, Dec. 2010 (Year: 2010).*
Girbau et al, Remote Sensing of Vital Signs Using a Doppler Radar and Diversity to Overcome Null Detection, IEEE Sensors JI, vol. 12, No. 3, Mar. 2012 (Year: 2012).*

* cited by examiner

NON-CONTACT SELF-INJECTION-LOCKED VITAL SIGN SENSOR

CROSS REFERENCE TO RELATED APPLICATION

This application claims the benefits of Taiwan application Serial No. 108116438, filed on May 13, 2019, the disclosures of which are incorporated by references herein in its entirety.

TECHNICAL FIELD

The present disclosure relates in general to a non-contact self-injection-locked vital sign sensor and, in particular, to a non-contact self-injection-locked vital sign sensor that can be made through low-cost integrated circuit (IC) fabrication process, but can still remain high frequency and exhibit high sensitivity, and can be used for vital sign detection/measurement.

BACKGROUND

Wearable vital sign sensors have become one of the most popular electronic devices in recent years. These devices can be used to detect vital signs of human beings, such as respiration, heart beats and pulse rates. The current wearable vital sign sensors detect vital signs mostly by applying photoelectric sensing. This method is performed by lighting a light beam on the skin of a human body, and by photoelectric devices for capturing the light beam to monitor the changes in the intensity of the light beam. If the intensity changes, it can be determined that the blood volume has changed, and that means that the heart has performed a contraction. The heart beats can thus be detected.

However, the method can be easily affected by ambient light, which makes that these kind of sensors must be in contact with human skin tightly for correct vital sign data. This restricts the design of vital sign sensors, such as many kinds of vital sign sensors should be designed as a wrist watch. Moreover, since these sensors must be in contact with human skin tightly, wearer may be uncomfortable after wearing these sensors for a long time.

In addition, with respect to non-contact self-injection-locked vital sign sensor, the operation frequency will also affect the sensitivity of the sensors. The higher the frequency, the higher the sensitivity. For example, the generally-adopted operation frequency is 2.4 GHz. It would exhibit lesser sensitivity, but the costs for the circuit structure is lower. For circuits with 5.8 GHz operation frequency, though higher sensitivity can be achieved, but the costs can be daunting. What could have happened when 24 GHz operation frequency and so on is adopted can be expected.

Further, frequency discriminators are widely seen in current non-contact self-injection-locked vital sign sensors for frequency demodulation. Frequency discriminator demodulate the modulated signals to retrieve vital signs. However, the size of a frequency discriminator appears to be too large, which is inappropriate for miniaturized devices. The operation frequency of a frequency discriminator cannot be raised easily either.

From the above descriptions, a "non-contact self-injection-locked vital sign sensor" that is of smaller size, that costs less, and that can be made through low-cost IC fabrication process but still remain the characters of high operation frequency, high sensitivity, is needed in the relevant technological field.

SUMMARY

An object of the present disclosure is to provide a non-contact self-injection-locked vital sign sensor. The non-contact self-injection-locked vital sign sensor includes: a transmission antenna for transmitting a radio frequency (RF) signal; a receiving antenna for receiving a reflected RF signal; a self-injection-locked integrated circuit electrically connected with the transmission antenna, including: a voltage-controlled oscillator for generating two oscillation RF signals with opposite phases; a mixer for receiving the two oscillation RF signals and the reflected RF signal, the two oscillation RF signals and the reflected RF signal being mixed in the mixer to generate a frequency-divided RF signal that is then sent to the voltage-controlled oscillator, wherein the voltage-controlled oscillator then generates a frequency- and amplitude-modulated signal; two amplifiers for receiving and amplifying the frequency modulated and amplitude modulated signal; and a harmonic-frequency power combiner for receiving and combining the two amplified RF signals and generating the frequency-multiplied RF signal for transmitting antenna, wherein the transmitting antenna transmits the frequency-multiplied RF signal to a living body, and the living body generates the reflected RF signal; a demodulator electrically connected with the self-injection-locked integrated circuit for receiving at least one of the frequency- and amplitude-modulated signals, and generating a vital sign; and a baseband amplifier electrically connected with the demodulator, for receiving and amplifying the vital sign, and generating a baseband signal.

BRIEF DESCRIPTION OF THE DRAWINGS

The present disclosure will become more fully understood from the detailed description given herein below and the accompanying drawings which are given by way of illustration only, and thus are not limitative of the present disclosure and wherein.

DETAILED DESCRIPTION

Figure 1:
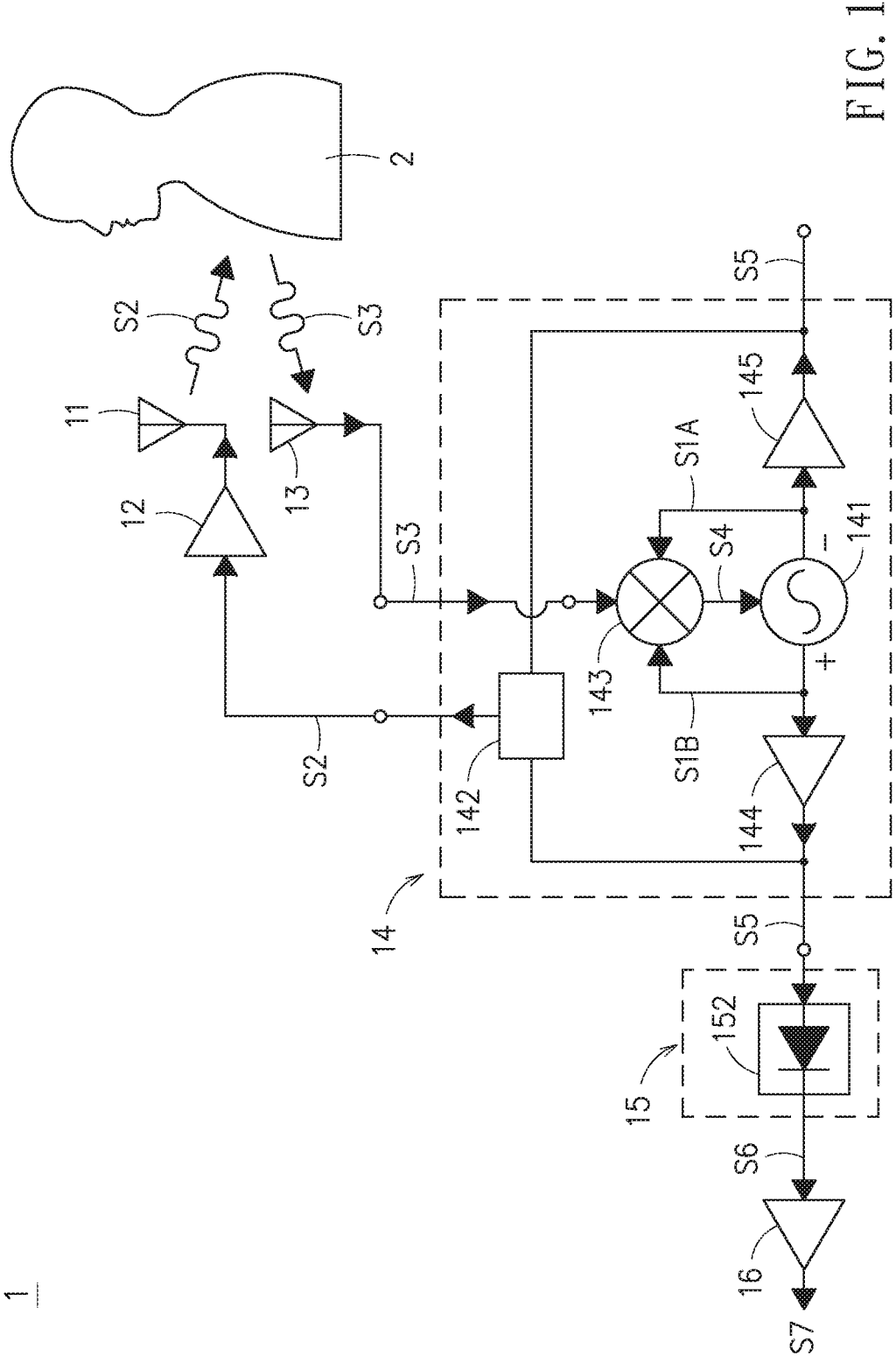
FIG. 1 is a schematic view of the structure of an embodiment of the present invention.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Reference is made to FIG. 1, in which a non-contact self-injection-locked vital sign sensor is depicted. The non-contact self-injection-locked vital sign sensor 1 includes a transmitting antenna 11, a power amplifier 12, a receiving antenna 13, a self-injection-locked integrated circuit 14, a demodulator 15 and a baseband amplifier 16. In the present embodiment, the demodulator 15 includes an envelope detector 152.

The operation principle of the present invention will be described in detail in the following. The self-injection-locked integrated circuit 14 transmits a radio frequency (RF) signal S2 to the power amplifier 12. The transmitting antenna 11 transmits the RF signal to a living body 2, and the living body 2 then generates a reflected RF signal S3 back to the self-injection-locked integrated circuit 14. The self-injection-locked integrated circuit 14 accordingly generates two frequency- and amplitude-modulated signals S5. The demodulator 15 receives at least one of the frequency- and amplitude-modulated signals, and generates a vital sign S6 that is then being sent to the baseband amplifier 16. The baseband amplifier 16 receives and amplifies the vital sign S6 and generates a baseband signal S7.

It should be noted that, the power amplifier 12 is disposed in between the transmitting antenna 11 and the self-injection-locked integrated circuit 14. The power amplifier 12 amplifies frequency (RF) signal S2 before it is sent to the transmitting antenna 11. The purpose of the amplifying is to enhance the RF signal S2, and also to increase effective detection distance of the vital sign for living body 2. In other words, if the RF signal S2 is strong enough, the power amplifier 12 may be omitted.

One of the technical characters of the present invention is that the self-injection-locked integrated circuit 14 is capable of performing frequency doubling and dividing, so that the self-injection-locked integrated circuit 14 can be made with low-cost IC fabrication process, but can still perform at high frequency and can still increase the sensitivity, which is appropriate for living body vital sign detection. In the present embodiment, the self-injection-locked integrated circuit 14 includes a voltage-controlled oscillator 141, a harmonic-frequency power combiner 142, a mixer 143 and two amplifiers 144, 145. The voltage-controlled oscillator 141, harmonic-frequency power combiner 142 and the mixer 143 are integrated in an IC to reach the demand of small size device.

Moreover, the power amplifier 12, the, self-injection-locked integrated circuit 14, demodulator 15 and baseband amplifier 16 can also be integrated into a single IC.

The voltage-controlled oscillator 141 is configured to generated two oscillation RF signals S1A, S1B with opposite phases. The mixes 143 is configured to receive the two oscillation RF signals S1A, S1B and the reflected RF signal S3. The oscillation RF signals S1A, S1B and the reflected RF signal S3 are mixed in the mixer 143 to generate a frequency-divided RF signal S4 that is then sent (injected) into the voltage-controlled oscillator 141. The voltage-controlled oscillator 141 then generates two frequency- and amplitude-modulated RF signals S5. The two amplifiers 144, 145 respectively receives the two frequency- and amplitude-modulated RF signals S5. The harmonic-frequency power combiner 142 receives and combines the two amplified RF signals S5 and generates the frequency-multiplied RF signal S2 for transmitting antenna 11. The transmitting antenna 11 transmits the RF signal S2 to the living body 2, and the living body 2 generates the reflected RF signal S3 which is received by the receiving antenna 13 for sending to the mixer 143.

The voltage-controlled oscillator 141 may generate two frequency- and amplitude-modulated RF signals S5, so that a user may choose either demodulator for demodulation. Both are with equivalent effectiveness. In the present embodiment, only the demodulator 15 is elected for demodulation.

The down-converter composed of the voltage-controlled oscillator 141 and the mixer 143 and the up converter composed of the amplifiers 144, 145 and the power amplifier 142 make special relations between the RF signals S1A and S1B, the frequency-multiplied RF signal S2, and the frequency-divided RF signal S4. The frequency of the frequency-multiplied RF signal S2 is X times of that of the RF signal S1A and SIB, and X is an integer greater than or equal to 2. The frequency of the reflected RF signal S3 is Y times of that of the divided RF signal S4, and Y is an integer greater than or equal to 2.

By different demands, X and Y can be any natural number, such as 2 or 3, or other natural numbers. X equals to Y. For example, RF signals S1A and S1B may be a 12 GHz signal. The harmonic-frequency power combiner 142 doubles the frequency it receives, the frequency-multiplied RF signal S2 is 24 GHz. The mixer 143 may divide the frequency of the signal it receives by 2, so that the frequency of the divided RF signal S4 is 12 GHz. The above description is only for exemplary purpose, it is not meant to limit the scope of the present invention.

Regarding the 24 GHz frequency, since the frequency band falls within the ISM frequency band, for which applying license for communication purpose is not needed, to detect vital sign of a living body can still be done if the operation frequency is changed (e.g., arbitrary X times of the operation frequency). However, the operation frequency could affect the sensitivity of a sensor. In the above description, a sensor operates at 2.4 GHz is taken for example. A sensor operating at 5.8 GHz performs better than a sensor operating at 2.4 GHz in terms of sensitivity.

Figure 2:
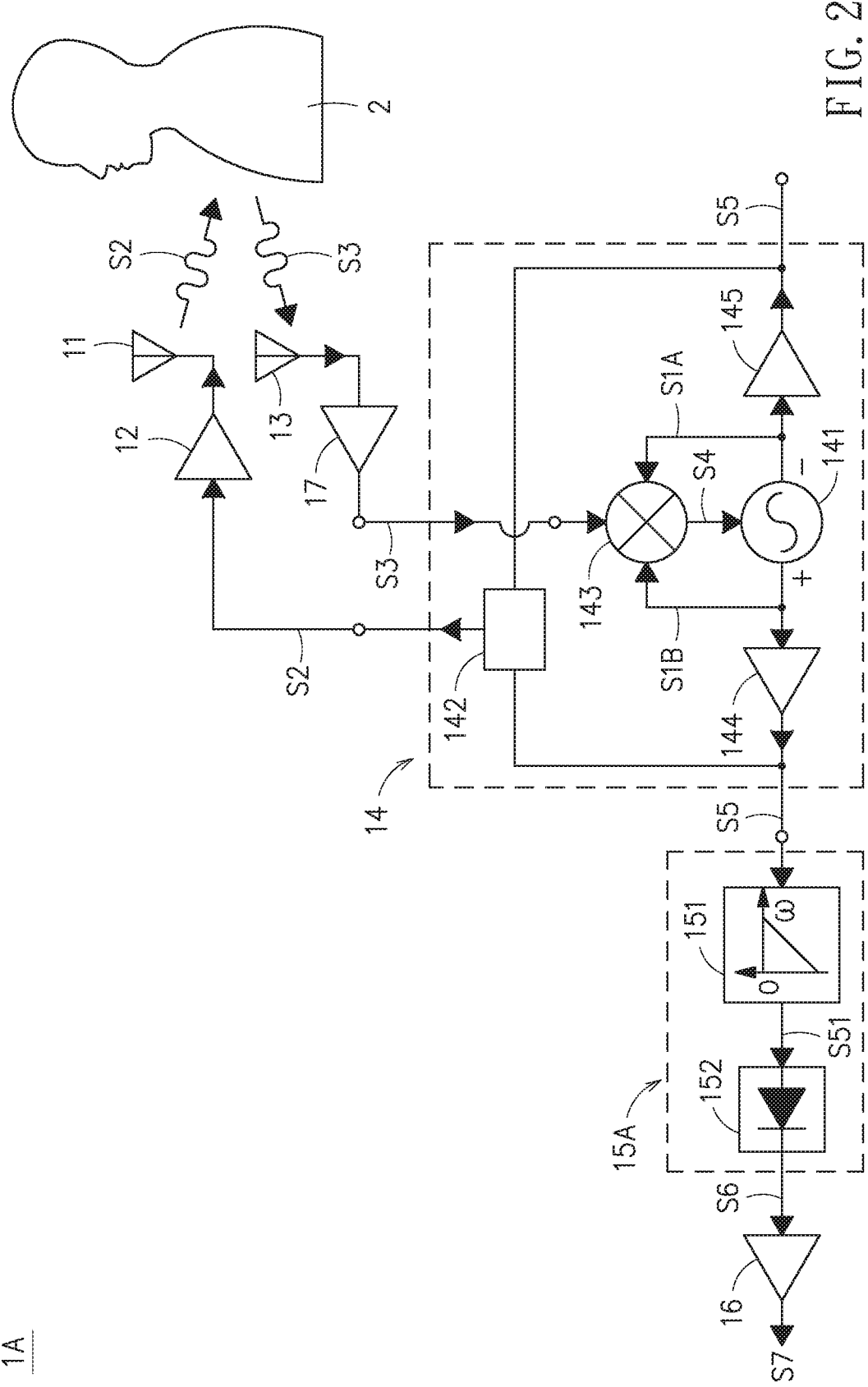
FIG. 2 is a schematic view of a demodulator of FIG. 1 having a differentiator, according to the embodiment of the present invention.

Reference is next made to FIG. 2, in which only differences from FIG. 1 will be described. In FIG. 2, a low noise amplifier 17 is disposed in between the transmitting antenna 11 and the self-injection-locked integrated circuit 14. The low noise amplifier 14 functions the as the power amplifier 12, that they are all for amplifying signals. The low noise amplifier 17 may amplify the reflected RF signal S3 received by the receiving antenna 13 and then send the signal to the mixer 143 of the self-injection-locked integrated circuit 14. The purpose is to enhance the reflected RF signal S3, and in the meantime to increase the effective detection distance of the vital sign to the living body 2. In other words, if the intensities of the frequency-multiplied radio frequency (RF) signal S2 and the reflected RF signal S3 are strong enough, the power amplifier 12 and the low noise amplifier 17 may be omitted.

Moreover, the demodulator 15A is implemented as a differentiator 151 electrically connected in between the self-injection-locked integrated circuit 14 and the envelope detector 152. The differentiator 151 receives the frequency- and amplitude-modulated signals S5 and differentiates these two signals, so as to transform the frequency-component of the frequency- and amplitude-modulated signals S5 into amplitude-modulated component. Therefore, the frequency- and amplitude-modulated signals S5 are transformed into differentiated frequency- and amplitude-modulated signals S51. The envelope detector 152 electrically connects with the differentiator 151 and receives the differentiated frequency- and amplitude-modulated signals S51. The envelope detector 152 performs amplitude demodulation on the differentiated frequency- and amplitude-modulated signals S51 to acquire the vital sign S6. Since the differentiator 151 of the present embodiment is utilized to transform a frequency modulated signal into an amplitude modulation signal, the sensitivity for micro vibrations that the living body 2 exhibit can be increased. The differentiator 151 may be a microstrip differentiator, and the operation frequency of the differentiator 151 is the same as those of the frequency- and amplitude-modulated signals S5.

It should be noted that the power amplifier 12, the low noise amplifier 17, the self-injection-locked integrated circuit 14, the demodulator 15A and the baseband amplifier 16 may be integrated into a single IC.

Figure 3:
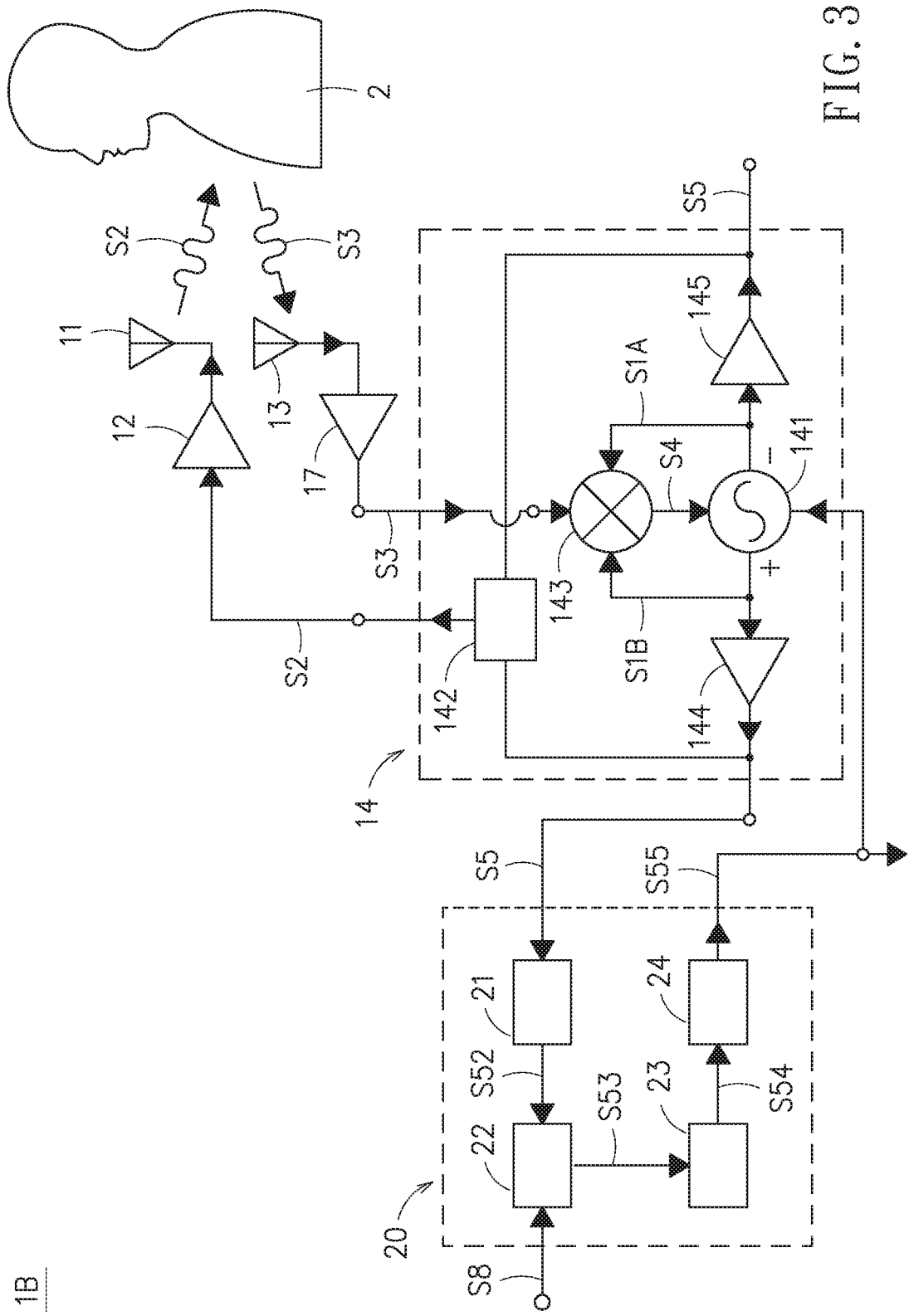
FIG. 3 is a schematic view of a demodulator being a phase-locked loop, according to the embodiment of the present invention.

Reference is next made to FIG. 3. In the present embodiment shown in FIG. 3, the self-injection-locked integrated circuit 14 connects with a phase-locked loop (PLL) 20.

The PLL 20 includes a frequency divider 21, a phase detector 22, a charge pump 23 and a loop filter 24. The frequency divider 22 is configured for receiving the frequency- and amplitude-modulated signals S5, and for dividing the frequency- and amplitude-modulated signals S5 to obtain a divided oscillation signal S52. The phase detector 22 is configured for receiving the divided oscillation signal S52 and a reference signal S8, and for comparing the divided oscillation signal and the reference signal, to make the phases of the divided oscillation signal S52 and a reference signal S8 to be the same. The charge pump 23 is configured for receiving a phase detected output signal S53 from the phase detector 22, and for transforming the phase detected output signal S53 into a current signal S54. The loop filter 24 is configured for receiving the current signal S54, and transforming the current signal S54 into an analog voltage signal S55 and filtering out high frequency noise, and the analog voltage signal S55 is then transmitted to the self-injection-locked integrated circuit 14.

By processing the control voltage signal S55, the vital sign of the living body 2 can be obtained. In other words, the control voltage is the vital sign of the living body 2. The output signal S53, current signal S54 and analog voltage signal S55 are all vital signs of the living body 2, but just in different signal forms.

It should be noted that the power amplifier 12, the low noise amplifier 17, the self-injection-locked integrated circuit 14 and the PLL 20 may be integrated into a single IC.

Figure 4:
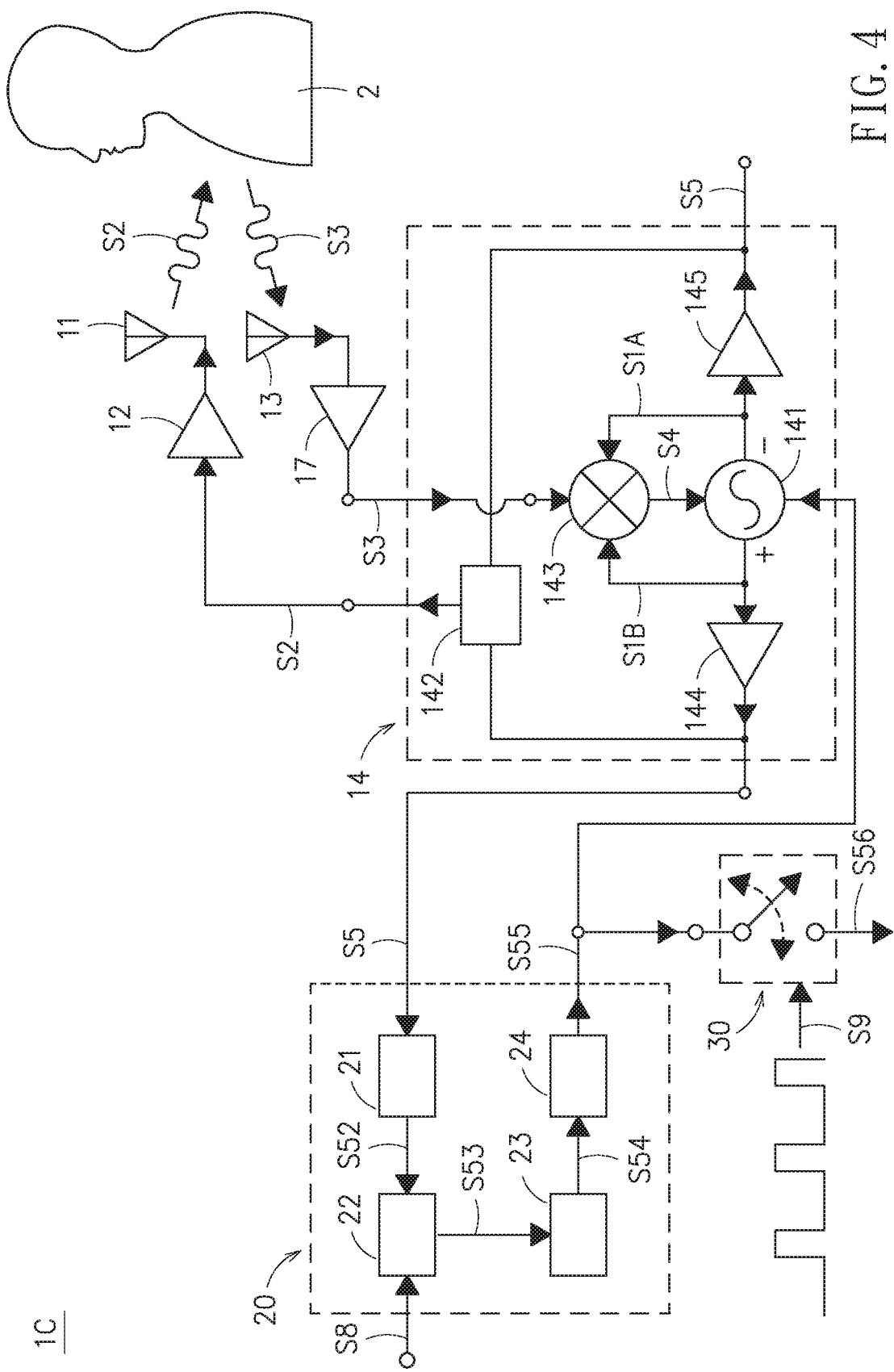
FIG. 4 is a schematic view of the structure of FIG. 3 in which a switch is applied.

Reference is next made to FIG. 4. In the present embodiment of FIG. 4, a witch 30 is connected in between the PLL 20 and the self-injection-locked integrated circuit 14. The switch 30 receives a control signal S9 (may be sent out from a signal processing device that is not shown in the figure, and switched, for generating a low intermediate frequency, IF) signal S56. An in-phase (I) signal channel vital sign and a quadrature (Q) signal channel vital sign are obtained after signal processing. In this regards, the null point measurement problem of the sensor can be solved, so that the sensor can measure signal at arbitrary positions.

It should be noted that the power amplifier 12, the low noise amplifier 17, the self-injection-locked integrated circuit 14, the PLL 20 and the switch 30 may be integrated into a single IC.

From the descriptions made to FIG. 1 to FIG. 4, different methods for demodulation can be flexibly adopted in the present invention.

In sum, since, through circuit design, that the voltage controlled oscillator, the mixer, the harmonic-frequency power combiner and the two amplifiers are all integrated into a single IC, the harmonic-frequency power combiner and the mixer can be sharing just one voltage controlled oscillator. In this regards, the size of the circuit and the cost for the circuit can be reduced. The circuit can be made through low-cost IC fabrication process, with high frequency and high sensitivity remain, and can be properly used for detecting vital sign of human bodies. It should be noted that solely using a harmonic-frequency power combiner for up-converting or solely using a mixer for down-converting is common in the field. However, either approach uses plenty transistors, which consume more energy, either has a bigger volume in terms of the IC circuit, and either costs more in terms of manufacturing.

To integrate a voltage controlled oscillator, a mixer, a harmonic-frequency power combiner and two amplifier into a single IC is unseen in the field, let alone to further apply the aforementioned integrated IC to vital sign detection. Therefore, to integrate a voltage controlled oscillator, a mixer, a harmonic-frequency power combiner and two amplifier into a single IC for vital sign detection/measurement should be having novelty in the relevant field.

With respect to the above description then, it is to be realized that the optimum dimensional relationships for the parts of the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present disclosure.

What is claimed is:

1. A non-contact self-injection-locked vital sign sensor, comprising:
   a transmitting antenna for transmitting a radio frequency (RF) signal;
   a receiving antenna for receiving a reflected RF signal;
   a self-injection-locked integrated circuit electrically connected with the transmitting antenna, including:
     a voltage-controlled oscillator for generating two oscillation RF signals with opposite phases;
     a mixer for receiving the two oscillation RF signals and the reflected RF signal, the two oscillation RF signals and the reflected RF signal being mixed in the mixer to generate a frequency-divided RF signal that is then sent to the voltage-controlled oscillator, wherein the voltage-controlled oscillator then generates a frequency- and amplitude-modulated signal;
     two amplifiers for receiving and amplifying the frequency- and amplitude-modulated signal; and
     a harmonic-frequency power combiner for receiving and combining the two amplified RF signals and generating a frequency multiplied RF signal for transmitting antenna, wherein the transmitting antenna transmits the frequency-multiplied RF signal to a living body, and the living body generates the reflected RF signal;
   a demodulator electrically connected with the self-injection-locked integrated circuit for receiving at least one of the frequency- and amplitude-modulated signals, and generating a vital sign; and
   a baseband amplifier electrically connected with the demodulator, for receiving and amplifying the vital sign, and generating a baseband signal.

2. The non-contact self-injection-locked vital sign sensor of claim 1, wherein the demodulator includes an envelope detector, and the envelope detector functions as an amplitude demodulator for the frequency- and amplitude-modulated signal.

3. The non-contact self-injection-locked vital sign sensor of claim 2, wherein the demodulator includes a differentiator, the differentiator electrically connects with the self-injection-locked integrated circuit, for receiving the frequency- and amplitude-modulated signal, the differentiator differentiates the frequency- and amplitude-modulated signal to transform the two signals into a differentiated frequency- and amplitude-modulated signal, the envelope detector electrically connects with the differentiator, and the envelope detector functions as an amplitude demodulator for the differentiated frequency- and amplitude-modulated signal.

4. The non-contact self-injection-locked vital sign sensor of claim 1, wherein the demodulator is a phase-locked loop, and the phase-locked loop includes:
- a frequency divider for receiving the frequency- and amplitude-modulated signals, and for dividing the frequency- and amplitude-modulated signals to obtain a divided oscillation signal;
- a phase detector for receiving the divided oscillation signal and a reference signal, and for comparing and outputting the divided oscillation signal and the reference signal;
- a charge pump for receiving a phase detected output signal from the phase detector, and for transforming the phase detected output signal into a current signal; and
- a loop filter for receiving the current signal, and transforming the current signal into an analog voltage signal and filtering out high frequency noise, wherein the analog voltage signal is transmitted to the self-injection-locked integrated circuit, and the control voltage is the vital sign.

5. The non-contact self-injection-locked vital sign sensor of claim 4, wherein a switch is disposed in between the phase-locked loop and the self-injection-locked integrated circuit, the switch receives a control signal for switching to generate a low intermediate frequency (IF), and an in-phase signal channel vital sign and a quadrature signal channel vital sign are obtained after signal processing.

6. The non-contact self-injection-locked vital sign sensor of claim 1, wherein the frequency of the frequency-multiplied RF signal is X times of that of the divided RF signal, and X is an integer greater than or equal to 2.

7. The non-contact self-injection-locked vital sign sensor of claim 6, wherein the frequency of the reflected RF signal is Y times of that of the divided RF signal, and Y is an integer greater than or equal to 2.

8. The non-contact self-injection-locked vital sign sensor of claim 7, wherein X equals to Y.

9. The non-contact self-injection-locked vital sign sensor of claim 1, wherein a power amplifier is disposed in between the transmitting antenna and the self-injection-locked integrated circuit for amplifying the frequency-multiplied RF signal.

10. The non-contact self-injection-locked vital sign sensor of claim 1, wherein a low-noise amplifier is disposed in between the transmitting antenna and the self-injection-locked integrated circuit for amplifying the reflected RF signal.

* * * * *